US011272855B2

(12) United States Patent
Vogel

(10) Patent No.: US 11,272,855 B2
(45) Date of Patent: Mar. 15, 2022

(54) METHOD AND DEVICE FOR DETERMINING THE BODY WEIGHT OF A PERSON

(71) Applicant: SECA AG, Reinach (CH)

(72) Inventor: Frederik Vogel, Hamburg (DE)

(73) Assignee: SECA AG, Reinach (CH)

( * ) Notice: Subject to any disclaimer, the term of this patent is extended or adjusted under 35 U.S.C. 154(b) by 304 days.

(21) Appl. No.: 16/191,258

(22) Filed: Nov. 14, 2018

(65) Prior Publication Data

US 2019/0099107 A1     Apr. 4, 2019

Related U.S. Application Data

(63) Continuation-in-part of application No. 14/114,594, filed as application No. PCT/DE2012/001024 on Oct. 17, 2012, now abandoned.

(30) Foreign Application Priority Data

Nov. 14, 2011 (DE) .................... 10 2011 118 998.3

(51) Int. Cl.
*A61B 5/00* (2006.01)
*A61B 5/0537* (2021.01)

(52) U.S. Cl.
CPC .......... *A61B 5/0537* (2013.01); *A61B 5/6825* (2013.01); *A61B 5/6829* (2013.01); *A61B 5/7278* (2013.01); *A61B 5/4872* (2013.01); *A61B 5/4875* (2013.01)

(58) Field of Classification Search
CPC ... A61B 5/6892; A61B 5/4872; A61B 5/0537; A61B 5/6825; A61B 5/7278; A61B 5/6829; A61B 5/4875

USPC .......... 600/300, 301, 547; 382/131; 702/173
See application file for complete search history.

(56) References Cited

U.S. PATENT DOCUMENTS

| 8,099,160 | B2* | 1/2012 | Kanai | A61B 5/0537 |
| | | | | 600/547 |
| 2006/0030783 | A1* | 2/2006 | Tsai | A61B 5/01 |
| | | | | 600/547 |
| 2008/0058610 | A1* | 3/2008 | Sato | A61B 5/4872 |
| | | | | 600/300 |
| 2009/0089672 | A1* | 4/2009 | Tseng | A61B 5/0537 |
| | | | | 715/700 |
| 2009/0182204 | A1* | 7/2009 | Semler | G16H 40/63 |
| | | | | 600/301 |
| 2010/0098310 | A1* | 4/2010 | Toth | G06T 7/0012 |
| | | | | 382/131 |
| 2010/0106045 | A1* | 4/2010 | Sato | A61B 5/4869 |
| | | | | 600/547 |
| 2010/0249642 | A1* | 9/2010 | Cha | A61B 5/0537 |
| | | | | 600/547 |

(Continued)

*Primary Examiner* — May A Abouelela
(74) *Attorney, Agent, or Firm* — Lucas & Mercanti, LLP; Klaus P. Stoffel

(57) ABSTRACT

A method and a device for determining an estimation value of the body weight of a person, in which at least one measurement value typical for a biological impedance measurement is determined and transmitted to an evaluation unit. The evaluation unit processes the measurement value together with individual or several individual data of the person as well as taking into consideration statistical data concerning other persons, in order to determine an estimated value for the weight of the person.

8 Claims, 2 Drawing Sheets

(56) References Cited

U.S. PATENT DOCUMENTS

| | | | | |
|---|---|---|---|---|
| 2010/0312074 A1* | 12/2010 | Sato | ............ | G01G 19/4146 |
| | | | | 600/300 |
| 2011/0112428 A1* | 5/2011 | Hsieh | ............ | A61B 5/7264 |
| | | | | 600/547 |
| 2011/0213268 A1* | 9/2011 | Kosaka | ............ | G01G 21/28 |
| | | | | 600/547 |
| 2011/0245710 A1* | 10/2011 | Jensen | ............ | A61B 5/6843 |
| | | | | 600/547 |
| 2011/0301916 A1* | 12/2011 | Oshima | ............ | G01G 19/50 |
| | | | | 702/173 |
| 2013/0072813 A1* | 3/2013 | Vogel | ............ | G01G 19/50 |
| | | | | 600/547 |
| 2013/0096456 A1* | 4/2013 | Fukuda | ............ | A61B 5/0537 |
| | | | | 600/547 |
| 2013/0131538 A1* | 5/2013 | Gaw | ............ | A61B 5/4878 |
| | | | | 600/547 |
| 2013/0197389 A1* | 8/2013 | Levin | ............ | A61B 5/0537 |
| | | | | 600/547 |
| 2014/0249384 A1* | 9/2014 | Levin | ............ | A61B 5/028 |
| | | | | 600/301 |

* cited by examiner

METHOD AND DEVICE FOR DETERMINING THE BODY WEIGHT OF A PERSON

CROSS-REFERENCE TO RELATED APPLICATIONS

The present application is a Continuation-In-Part Application of U.S. patent application Ser. No. 14/114,594, filed Oct. 29, 2013, which is a 371 of International Application PCT/DE2012/001024 filed on Oct. 17, 2012 which claims the benefit of priority from German Patent Application No. 10 2011 118 998.3 filed Nov. 14, 2011, the contents of each of which are incorporated herein by reference.

BACKGROUND OF THE INVENTION

The invention relates to a method for measuring the body weight of a person, wherein by means of measuring technology at least one parameter typical for a biological impedance measurement is determined and is transmitted to an evaluation unit.

Moreover, the invention relates to a device for determining the body weight of a person, wherein the device includes at least one sensor for determining at least one parameter typical for a biological impedance measurement, and wherein the sensor is coupled to an evaluation unit.

In a predominant number of persons, the weight measurement can be carried out in a simple manner by having these persons stand on a scale and the corresponding body weight is indicated. The weight measurement has been found problematic in bed-ridden patients and/or patients who require aid. However, it is particularly with these persons that the determination of the body weight is of special significance in order to be able to draw conclusions concerning the nutritional state. Frequently in the case of such persons, there is the problem that these persons become overnourished or undernourished, which leads to undesirable weight gains or losses. Similarly, there may be the problem that lack of movement and stimulation lead to a loss of muscle.

In order to measure the body weight of such persons, it is frequently necessary to lift and/or move the patients out of the bed. Inasmuch as possible, the persons are then placed on a scale or are weighed in a sitting position. Even more complicated is the determination of the body weight by weighing the bed together with the patient and then correspondingly determine the weight of only the bed. Such a sequence is also subject to significant difficulties since especially in persons requiring aid the beds are frequently not easily accessible from all sides. Moreover, the patients are frequently connected to measuring or medical supply devices whose own weight also has to be taken into consideration.

Accordingly, the previous work sequences in the determination of the body weight of bed-ridden patients may be labor intensive, imprecise, and for the patient at least unpleasant and frequently even painful.

SUMMARY OF THE INVENTION

Therefore, it is the object of the present invention to improve a method of the type mentioned in the introduction in such a way that the weight determination is reinforced in lying or sitting patients.

In accordance with the invention, this object is met in that the evaluation unit processes the measurement value together with individual and several additional individual data of the person and, taking into consideration statistical data concerning other persons determines an estimated value for the weight of the person which is as accurate as possible.

Another object of the present invention is to construct a device of the type mentioned in the introduction in such a way that the determination of the weight of lying persons is supported.

In accordance with the invention, this object is met in that the evaluation unit is enabled to access an individual storage unit for individual data of the person as well as a reference storage unit for statistical data of other persons, and that, for interconnecting the measuring parameters, the evaluation unit is constructed with contents of the individual storage unit as well as with contents of the reference storage unit.

In a preferred embodiment of the invention the evaluation unit comprises a processing device.

The method according to the invention and the device make it possible to determine the nutritional state of a patient without knowing the exact actual weight of the patient. Consequently, it is particularly possible to represent gains or losses in the body weight. This can take place with or without a serial measurement. In particular, it is possible to determine the weight of the patient without having to move the patient.

A determination of the measurement value can be effected preferably with the use of a so-called Body Composition Analyzer (BCA). For example, such a device is capable of determining the weight proportions of muscles, fat, water and bones within the human body. In this regard, typically further characterizing values of the respective person are taken into consideration as influencing parameters, for example, the age, the gender, as well as the ethnicity. Other parameters considered by embodiments of the invention are the height (total body or body segments), circumferences of part of the body. Additionally, the obvious body and/or health condition may be considered as part of the algorithm modifying the coefficients or formulas in dependency of the judgement whether the individual should be categorized as a muscular/athletic, a normal/medium trained, a skinny or an obese individual. The weight of the respective person is usually determined by a weighing process. Accordingly, in the case of a conventional use of such a BCA device, the weight of the person is taken into consideration as an influencing parameter of an evaluation algorithm. Actual measurement values of the BCA device are impedance values of the body between predetermined measuring points. The measuring points are typically found in the areas of the hands or the feet of the respective person.

In accordance with the invention, the functional dependency of the values of the parameters determined by the BCA device on the weight of the person is utilized, mathematically speaking, for determining this weight through a resolution of the respective functional dependency according to the weight. The accuracy of the determination of the weight can be improved by additionally considering statistical data of comparison persons.

For the BCA several different methods of bioelectrical impedance analysis are applicable. In a first method, namely single frequency body impedance analysis (SF-BIA), surface electrodes are commonly placed on hand and foot of an individual. The impedance measurement of the individual's tissues in between the electrodes is taken at a single frequency, generally at 50 kHz. SF-BIA allows to estimate the fat-free mass and the dry body weight, but is not applicable for determining differences regarding the intra-cellular water.

In a second method, namely multi-frequency body impedance analysis (MF-BIA), impedance measurements are taken at multiple frequencies, commonly at 0, 1, 5, 50, 100 and 200 to 500 kHz) to allow estimations for the fat-free mass, the dry body weight, the infra-cellular and the extra-cellular water in the tissues in between the surface electrodes connected to the individual's body.

In a third method, namely bioelectrical spectroscopy (BIS), mathematical modeling and mixture equations, as for example the Cole-Cole plot, are utilized to generate relations between the frequency dependent impedance values and body fluid compartments to allow predictions of the impedance at 0 kHz and the impedance at an infinite frequency. These values are then used to calculate body composition data by plugging them into prediction equations.

Each of the before mentioned methods of bioelectrical impedance analysis is applicable to estimate values for the whole body or body compartments/components mainly based on the placement of the surface electrodes.

In a preferred embodiment of the invention MF-BIA is applied to gather the bioimpedance measurement values required for the prediction process according to the invention.

An increased accuracy in the determination of the estimated values for the weight of the person can be achieved in that the evaluation unit takes into consideration at least one additional measuring value which is in the past with respect to time.

In particular, it is being considered to carry out a serial measurement.

The gathered bioimpedance data is then used together with the at least one additional datum to calculate body composition data as the total body water, the fat-free mass of the body and/or the total body weight of the individual.

The method and the device according to the invention are applicable in several medical use cases. Exemplary use cases are described hereafter.

In a first use case the hydration of an individual is determined with a method and/or a device according to the invention to identify over- or underhydration of the individual for example given by a patient in the intensive care unit of a hospital.

Surface electrodes are placed on at least one hand of the individual and on at least one foot of the individual and the bioimpedance is measured at a frequency of 50 kHz. The bioimpedance measurement value consists of the two components real part R and imaginary part Xc.

Additional data of the individual is loaded into the system either by the medical (care) personnel using the human machine interface of the method or device according to the invention or by automatically loading the required data from the digital patient file stored on a local storage unit incorporated by the device according to the invention or on a network storage unit accessible via wired or wireless communication interfaces.

In the following with regard to all examples "calculation" means to obtain the related parameter by an implementation of the specific formula in a device for effecting functional calculation. For example, a processing device realized by a microchip may be used as such a device.

In the first use case the height, the age and the sex are loaded into the system.

The total body water (TBW) is then calculated by the formula $$TBW = a * \frac{height^2}{R} - b * Xc - c * age + d * sex - e.$$

The parameter sex is defined as 1 for male individuals an as 2 for female individuals. The coefficients a, b, c, d and e are defined as a=0.59, b=0.22, c=0.024, d=0.41 and e=6.2 in an exemplary embodiment of the invention.

In an alternative embodiment of the invention the length of the lower leg or the knee-height is used instead of the total height of the individual since a more accurate, easier measurement is allowed for bed-ridden persons. In this alternative embodiment of the invention the total body water of an individual is estimated by the formula $$TBW = f - g * age + h * \text{length of the lower leg}.$$

For a male individual the coefficients are defined as f=64.2, g=0.04 and h=2.02 and for a female individual the coefficients are defined as f=84.9, g=0.25 and h=1.83 in an exemplary embodiment of the invention.

Alternatively, a modified formula can be applied in which the knee-height can directly be plugged in. The formulas are modified for individuals of different ethnicities in other preferred embodiments of the invention.

In a second use case the fat-free mass of an individual is determined by a method and/or device according to the invention for example to allow to draw conclusions to the status of nutrition of a sarcopenia patient. The fat-free mass can be used as an indicator for the muscle mass, which is reducing over time for sarcopenia patients.

In a preferred embodiment of the invention the formula $$FFM = \frac{TBW[i]}{i}$$

Is used to estimate the fat-free mass based on the total body water in liters of the individual. The coefficient i is defined as 0.732 in an exemplary embodiment of the invention.

In an alternative embodiment the fat-free mass is determined with an estimation formula independent of the total body water.

In a third use case the method and/or the device according to the invention is used to determine the total body weight of an individual.

In a first embodiment of the invention related to the third use case the individuals total body weight is initially measured with a scale.

Close in time to the weight measurement with the scale a bioimpedance measurement is taken.

With the fat-free mass being estimated based on the bioimpedance value(s) for example according to at least one of the above-mentioned formulas and the total body weight it is possible to calculate the fat mass of the individual by subtracting the fat-free mass from the total body weight. This initially estimated fat mass is used as a reference for further measurements.

In the following measurements only a bioimpedance measurement is taken without measuring the weight of the individual using a scale. Assuming the fat-free mass is more volatile compared to the fat mass, the total body weight of the individual can be estimated as the sum of the fat-free mass determined with the bioimpedance measurement values of a following measurement and the reference fat mass.

In an alternative embodiment of the invention related to the third use case the change of the fat mass over time is considered for the estimation of the total body weight. The change of the fat mass is interpolated corresponding to the change of the fat-free mass in one embodiment of the invention. In another embodiment of the invention the time and/or the change of the fat-free mass are observed to indicate whether a new measurement of the total body weight using a scale is necessary to generate a new reference value for the fat mass.

In another fourth use case the total body weight of a person is estimated using a method and/or a device according to the invention without using a scale.

Additional parameters required to allow a satisfying estimation of the total body weight are for example the abdominal girth, the circumference of the upper arm and/or the upper leg. Generally additional parameters allowing an estimation of the fat mass are used according to one embodiment of the invention.

In a preferred embodiment of the invention related to use case four the abdominal girth is used for the estimation of the total body weight. The total body weight is estimated by the formula $$\text{total body weight} = j * \frac{height^2}{R} + k * R + l * \text{abdominal girth} - m * \text{age} + n * \text{sex} - o$$

In another preferred embodiment of the invention, wherein the coefficients are defined as j=0.79, k0.045, l=0.81, m=0.17, n=5.2 and o=65.

In an alternative embodiment of the invention related to the fourth use case the knee-height is used instead of the total height.

Preferred embodiments of the invention include combinations of the above presented features for the different use cases.

In an embodiment of the invention the evaluation unit is not part of the sensor for determining at least one parameter typical for a biological impedance measurement.

In a preferred embodiment of the invention the evaluation unit is incorporated by the sensor for determining at least one parameter typical for a biological impedance measurement.

In another preferred embodiment of the invention the sensor for determining at least one parameter typical for a biological impedance measurement is given by a body impedance analyzer.

In one embodiment of the invention four electrodes to determine body impedance values are incorporated by the sensor.

In another embodiment of the invention eight electrodes to determine body impedance values are incorporated by the sensor.

In a preferred embodiment of a method for determining the body weight of a person according to the invention in a first step the electrodes of the sensor device given by a body impedance analyzer are connected to the patient in the region of the hands and feet of the patient at least in the region of one hand and in the region of one foot of the person.

In a next step at least one bioimpedance value of the patient is determined. In a preferred embodiment of the invention MF-BIA is applied such that multiple bioimpedance values at different frequencies are determined.

In another step individual data of the patient is loaded into the system either by manual user input into the system or by automatically loading the relevant individual data for example from a digital patient file stored in a storage unit. The storage unit may be incorporated by the evaluation unit or the sensor (bio impedance analyzer) or being built as a network storage unit being accessible by the evaluation unit via a wired or wireless network connection.

According to the individual patient data an appropriate evaluation algorithm is selected out of a predefined number of evaluation algorithms and/or a predefined evaluation algorithm is adapted based on the individual patient data.

In another step statistical data/population data is loaded into the system either from a local storage unit or from a network storage unit and the evaluation algorithm adapted according to the statistical data. In a preferred embodiment of the invention the population data is selected based on the individual data of the patient.

In one embodiment of the invention the evaluation algorithm is selected based on the available individual patient data, e.g. if the age, the sex and total body height are available another formula is selected compared to the case if age, sex and the length of the lower leg are available and the evaluation algorithm is adapted based on the population data in dependency of the statistical data in modifying the coefficients of the formula.

In a next step of the method the at least one determined bioimpedance value is transmitted from the sensor to the evaluation unit via a wired or a wireless communication interface.

In a next step of the invented method the at least one determined bioimpedance value is plugged into the selected and modified formula and the estimation of the total body water, the fat-free mass and/or the total body weight is/are calculated.

In a next step of the invention the calculated the total body water, the fat-free mass and/or the total body weight is being displayed on a display of the system.

In a preferred embodiment the total body water, the fat-free mass and/or the total body weight is/are saved to the local and/or network storage unit such that the digital patient file is being updated accordingly.

In a preferred embodiment of the invention an application for determining the body weight of a person is being provided for installation on a body impedance analyzer.

In another preferred embodiment of the invention an application for determining the body weight of a person is being provided for installation on the evaluation unit or on the device incorporating the evaluation unit.

In an embodiment of the invention the application for determining the body weight of a person is automatically activated as soon as a bioimpedance measurement is started.

In another preferred embodiment of the invention the individual patient data and/or the statistical data is automatically loaded from the local or the network storage unit as soon as the required data is available for the system.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

BRIEF DESCRIPTION OF THE DRAWING

In the drawings, embodiments of the invention are schematically illustrated. In the drawing.

DETAILED DESCRIPTION OF THE INVENTION

Figure 1:
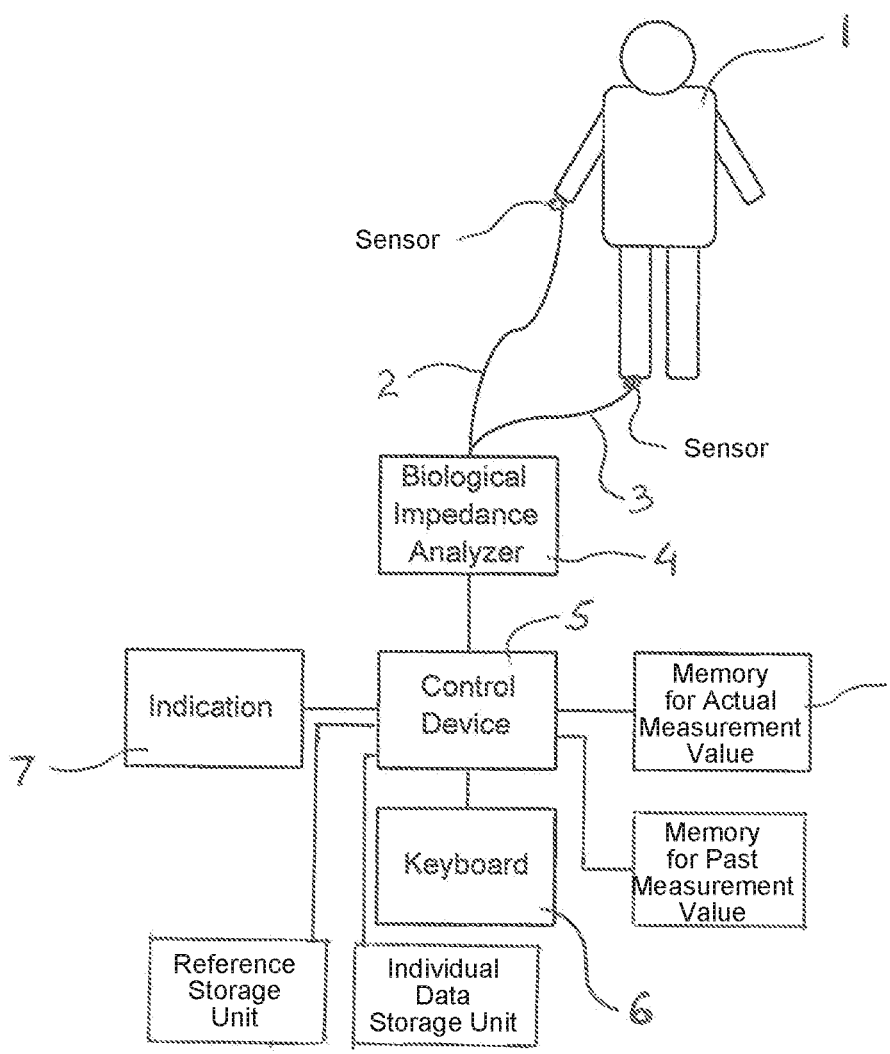
FIG. 1 is a schematic block diagram for illustrating the basic structure of the device used.
Figure 2:
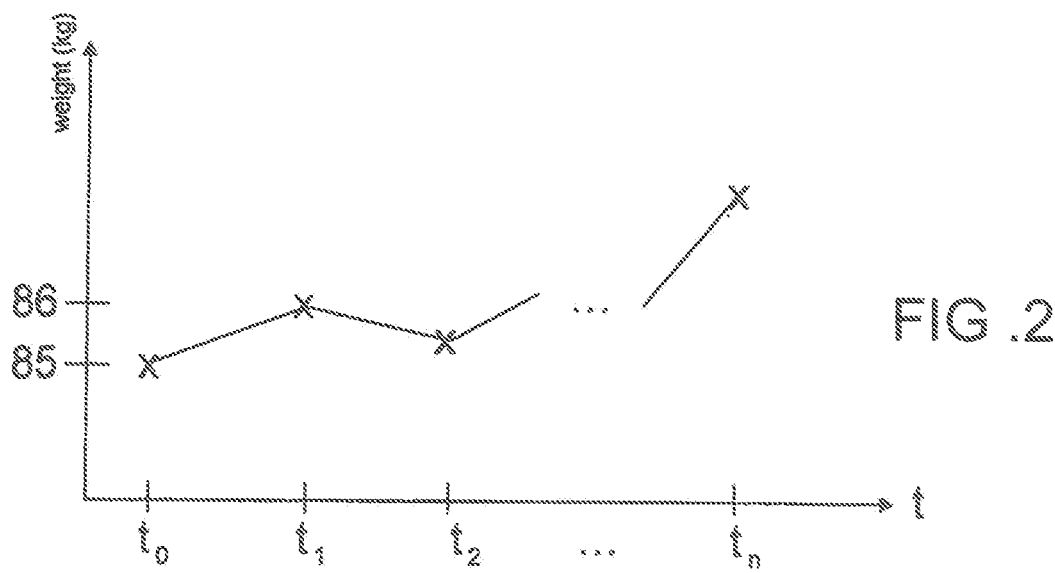
FIG. 2 shows as an example an illustration of a pattern of the body weight plotted over time.
Figure 3:
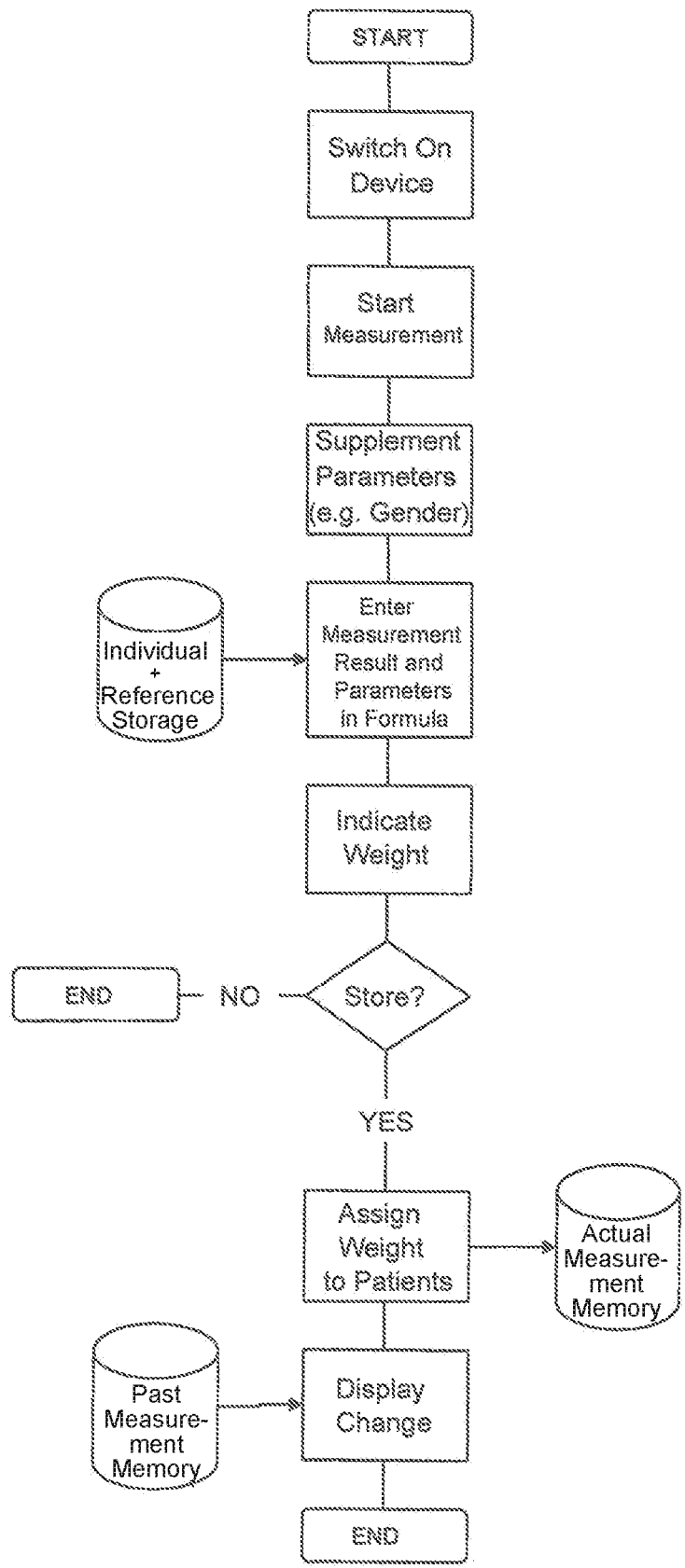
FIG. 3 is a sequence diagram for illustrating the operation of the method according to the invention.

FIG. 1 schematically shows a person 1 who is connected in a lying state through measuring cables 2, 3 to a measuring device 4. The measuring device 4 is connected to a control device 5. Typically, the control device 5 makes an evaluation unit available.

For facilitating operating input, the control device 5 may be coupled to a keyboard 6. Alternatively, other input devices can also be used.

Moreover, the control device 5 is connected to a display 7 and a storage unit 8.

In accordance with a typical process sequence, the respective person is measured at a first point in time (T0) with the use of the device according to the invention. This value is stored in the device, preferably with an assignment of an unequivocal identification number of the respective patient. If an actual weight of the patient should be known from a point in time (TP) further back, this actual last known weight can be taken into consideration.

In accordance with a preferred manner of carrying out the method, serial measurements at points in time (TX) are measured against values of the point in time (T0). This reinforces carrying out a serial measurement as well as a serial illustration. This makes it possible for an aide of the patient to recognize whether the state of nutrition of the patient is changing. In particular, this can be done without knowing the actual exact value of the body weight.

For documenting the respective measurement results, it is possible to equip the device with a printer. In addition, it is possible to carry out continuous measurements. With respect to the technical construction, the device may be portable or stationary.

While specific embodiments of the invention have been shown and described in detail to illustrate the inventive principles, it will be understood that the invention may be embodied otherwise without departing from such principles.

I claim:

1. A method for scalelessly determining an estimation value of current actual total body weight of a body of a human person, comprising the steps of:
determining with electrodes configured to be positioned on both hands and both feet of the body of the human person at least one measurement value for biological impedance measurements; transmitting the measurement value of the biological impedance measurements to an evaluation unit; processing the measurement value in the evaluation unit together with at least one additional datum of the human person and determining an estimated value for the current actual total body weight of the human person, taking into consideration predetermined statistical data concerning other human persons, wherein the processing step includes using the measurement value of the biological impedance measurements as well as the predetermined statistical data and the additional datum to determine the estimated current actual total body weight value of the human person, and further includes evaluating a correlation between the measurement value of the biological impedance measurements and the current actual total body weight of the human person, wherein measurement values of the biological impedance measurements taken temporally at least at two different points in time are evaluated and compared in the evaluation unit in determining the estimated value for the current actual total body weight, wherein one of the points in time is in real time and another of the points in time is an earlier point in time; and displaying the estimated value for the current actual total body weight, wherein the measurement value is determined using a body impedance analyzer (BIA), wherein actual measurement values of the (BIA) are impedance values of the body comprising real parts and imaginary parts between predetermined measurement points of the body, and wherein a functional dependency of parameters determined by the (BIA) on the current actual total body weight of the human person is utilized for resolving a functional relationship according to the current actual total body weight, wherein a temporal course of the real parts of the measured impedance values is evaluated, the method further comprises providing an application for determining the current actual total body weight of the human person for installation on the evaluation unit or a device incorporating the evaluation unit.

2. The method according to claim 1, wherein the evaluation unit additionally takes into consideration at least one past measurement with respect to time.

3. The method according to claim 1, including carrying out a serial measurement.

4. The method according to claim 1, wherein the at least one parameter for biological impedance measurements is taken with a multi-frequency body impedance analyzer.

5. The method according to claim 1, wherein the evaluation unit is incorporated in a sensor and the sensor being part of the body impedance analyzer.

6. A device for scalelessly determining current actual total body weight of a body of a human person, comprising: electrodes configured to be positioned on both hands and on both feet of the body of the human person for determining at least one measurement value for a biological impedance measurement; an evaluation unit coupled to a sensor, wherein the evaluation unit is enabled to access an individual storage unit for individual data of the human person and a reference storage unit for predetermined statistical data concerning other human persons, the evaluation unit being configured to link the at least one biological impedance measurement value to contents of the individual storage unit as well as to contents of the reference storage unit to determine an estimated value for the current actual total body weight of the human person based only on an evaluation of the biological impedance measurement, the individual data and the predetermined statistical data, wherein the evaluation unit is operative to use the at least one measurement value of the biological impedance measurement as well as the statistical data and the individual data for determining the estimated value for the current actual total body weight of the human person by evaluating a correlation between the measurement value of the biological impedance measurement and the current actual total body weight of the human person, wherein the evaluation unit is operative to take biological impedance measurement values temporally from at least two distinct points in time in determining the estimated value for the current actual total body weight of the human person, wherein one of the points in time is in real time and another of the points in time is an earlier point in time; and a display that indicates the estimated value for the current actual total body weight of the human person, wherein the evaluation unit is connected to a body impedance analyzer (BIA) that determines the measurement value, wherein actual measurement values of the (BIA) are impedance values of the body comprising real parts and imaginary parts between predetermined measurement points of the body, and wherein a functional dependency of parameters determined by the (BIA) on the current actual total body weight of the person is utilized for resolving a functional relationship according to the current actual total body weight, wherein a temporal course of the real parts of the measured impedance values is evaluated.

7. The device according to claim 6, wherein the evaluation unit is incorporated in the sensor.

8. The device according to claim 6, wherein the sensor is part of the body impedance analyzer.

* * * * *